United States Patent
Kaga et al.

(10) Patent No.: US 8,003,832 B2
(45) Date of Patent: Aug. 23, 2011

(54) PROCESS FOR RECOVERING PENTAFLUOROETHANE, AND PRODUCTION METHOD OF PENTAFLUOROETHANE INVOLVING THE PROCESS

(75) Inventors: Kazunari Kaga, Kawasaki (JP); Hiromoto Ohno, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 831 days.

(21) Appl. No.: 11/997,068

(22) PCT Filed: Jul. 27, 2006

(86) PCT No.: PCT/JP2006/315361
§ 371 (c)(1),
(2), (4) Date: Jan. 28, 2008

(87) PCT Pub. No.: WO2007/013680
PCT Pub. Date: Feb. 1, 2007

(65) Prior Publication Data
US 2010/0286456 A1  Nov. 11, 2010

(30) Foreign Application Priority Data
Jul. 28, 2005  (JP) .................................. 2005-218951

(51) Int. Cl.
*C07C 17/38*  (2006.01)
*C07C 17/20*  (2006.01)
(52) U.S. Cl. .......................... 570/178; 570/170; 570/177
(58) Field of Classification Search .................. 570/177, 570/178
See application file for complete search history.

(56) References Cited

U.S. PATENT DOCUMENTS

| 5,679,876 | A  | 10/1997 | Hub et al. |
| 6,457,327 | B1 | 10/2002 | Fidkowski et al. |
| 6,921,428 | B2 | 7/2005  | Yamamoto et al. |
| 7,074,974 | B2 | 7/2006  | Kaga et al. |
| 7,138,553 | B2 | 11/2006 | Ohno et al. |
| 2005/0065385 | A1 | 3/2005 | Kaga et al. |

FOREIGN PATENT DOCUMENTS

| JP | 48-10444    |    | 4/1973  |
| JP | 48-43326    |    | 12/1973 |
| JP | 56-166128   | A  | 12/1981 |
| JP | 2-40216     | A  | 2/1990  |
| JP | 2-48529     | B2 | 10/1990 |
| JP | 8-143486    | A  | 6/1996  |
| JP | 8-301801    | A  | 11/1996 |
| JP | 9-12487     | A  | 1/1997  |
| JP | 9-511515    | A  | 11/1997 |
| JP | 98/32521    | A  | 7/1998  |
| JP | 2000-117051 | A  | 4/2000  |
| JP | 2002-13872  | A  | 1/2002  |
| JP | 2003-190744 | A  | 7/2003  |
| JP | 2003-261476 | A  | 9/2003  |
| JP | 3470180     | B2 | 9/2003  |
| JP | 2003-286207 | A  | 10/2003 |
| WO | 95/27688    | A1 | 10/1995 |
| WO | 96/06063    | A1 | 2/1996  |
| WO | 96/11176    | A1 | 4/1996  |
| WO | 96/24569    | A1 | 8/1996  |

*Primary Examiner* — Jafar Parsa
(74) *Attorney, Agent, or Firm* — Sughrue Mion, PLLC

(57) ABSTRACT

The process for recovering pentafluoroethane of the invention includes bringing a mixed gas containing pentafluoroethane and a non-condensable gas into contact with a chlorinated solvent, and allowing the chlorinated solvent to absorb pentafluoroethane contained in the mixed gas. The process for the production of pentafluoroethane of the invention uses the recovering process.

12 Claims, No Drawings

PROCESS FOR RECOVERING PENTAFLUOROETHANE, AND PRODUCTION METHOD OF PENTAFLUOROETHANE INVOLVING THE PROCESS

TECHNICAL FIELD

The present invention relates to a process for recovering pentafluoroethane. The invention is also concerned with a process for producing pentafluoroethane wherein a chlorinated solvent containing pentafluoroethane that is recovered by the recovering process is used as a raw material for the production of pentafluoroethane.

BACKGROUND ART

Pentafluoroethane is a hydrofluorocarbon (HFC), a useful alternative of chlorofluorocarbons (CFC) and hydrochlorofluorocarbons (HCFC). It is widely used as low-temperature refrigerants, foaming agents, propellants and etching gases.

HFC contain substances having a global warming potential (GWP) several thousand times greater than carbon dioxide gas. This problem has been pointed out recently and HFC emissions have been increasingly controlled.

The emissions of pentafluoroethane will be generally attributed to:

(1) used refrigerants in scrapped refrigerators and the like; and (2) exhaust gases from the manufacturing process of semiconductors.

In the case (1), pentafluoroethane, which is emitted as used refrigerants when refrigerators are scrapped, is a condensable liquefied gas that is a mixture of pentafluoroethane and refrigerant oil. It maybe liquefied by compression or cooling and be easily recovered in a closed vessel.

In the case (2), however, exhaust gases from the semiconductor manufacturing are often mixtures of pentafluoroethane and large amounts of non-condensable diluent gases. Recovering pentafluoroethane from such mixed gases by the method in the case (1) is difficult.

The production of pentafluoroethane often generates pentafluoroethane diluted with large amounts of non-condensable gases, in which case it is difficult to recover pentafluoroethane. Such mixed gases are therefore frequently decomposed or combusted instead of recovering pentafluoroethane, but these treatments are not economical. Various methods are proposed for recovering pentafluoroethane that is diluted with large amounts of non-condensable gases.

Membrane separation is one of such methods proposed. JP-B-H02-48529 discloses separation using a permselective composite membrane, which includes a porous support membrane and an active thin membrane formed thereon by crosslinking a crosslinkable silicone resin. Japanese Patent No. 3470180 discloses separation using a gas permeation membrane that comprises a polymer based on poly(4-methylpentene-1). JP-A-2003-190744 discloses separation with a separation membrane that is obtained by carbonizing a polymer. JP-A-2001-510395 discloses separation using an inorganic molecular sieve membrane. However, these methods entail complicated processes because of short membrane life, time degradation of membranes which causes intricate controlling of separation conditions, and the need of eliminating beforehand membrane-degrading components in the gas to be treated. Moreover, separation membranes should be exchanged frequently to maintain a sufficient separation performance, increasing the cost.

Activated carbons are known to adsorb organic substances in exhaust gases. However, the existing adsorbents do not have an adequate adsorption capacity enough for recovering pentafluoroethane. To reuse pentafluoroethane that is recovered, it should be released from the adsorbent, which requires large-scale facility with heating and cooling functions and large amounts of energy to cause economical disadvantages.

Recovering organic substances by absorption in solvents is proposed. JP-A-H02-40216 discloses an absorbent composition based on polyethylene glycol dialkyl ether. After pentafluoroethane is recovered using this absorbent composition, however, to reuse pentafluoroethane that is recovered, it should be separated from the absorbent composition. As is the case for recovering with the adsorbents, this purification requires large-scale facility with heating and cooling functions and large amounts of energy to cause economical disadvantages. JP-A-2000-117051 discloses a process in which a chemically stable fluoride that is a gas at room temperature is recovered by being dissolved in a fluoride that is liquid at room temperature. This process requires purification for separating pentafluoroethane, and the fluorides that are liquid at room temperature are very expensive. JP-A-2002-13872 discloses a process in which a diluted gas containing a fluorocompound is brought into contact with a low-temperature liquid at not more than $-101°$ C. to recover the fluorocompound. However, cooling a solvent to such extremely low temperatures of $-101°$ C. or below requires a large amount of energy, and the fluorocompound recovered by this process has a low concentration and needs a further treatment.

OBJECT OF THE INVENTION

The present invention is directed to solving the above problems in the art. It is therefore an object of the invention to provide a novel process for recovering pentafluoroethane, and a process for the production of pentafluoroethane using the recovering process.

DISCLOSURE OF THE INVENTION

The present inventors diligently studied processes for recovering pentafluoroethane from a mixed gas containing pentafluoroethane and non-condensable gases which occurs for example by distillation in the production of pentafluoroethane. Consequently, it has been found that when the mixed gas is brought into contact with a chlorinated solvent, the chlorinated solvent absorbs pentafluoroethane and pentafluoroethane is recovered, thereby solving the aforesaid problems. The chlorinated solvent including pentafluoroethane has been found to be usable as a raw material in the production of pentafluoroethane, enabling more economical production of pentafluoroethane. The present invention has been completed based on the findings.

The present invention is concerned with the following [1] to [13].

[1] A process for recovering pentafluoroethane, comprising bringing a mixed gas containing pentafluoroethane and a non-condensable gas into contact with a chlorinated solvent to allow the chlorinated solvent to absorb pentafluoroethane contained in the mixed gas.

[2] The process for recovering pentafluoroethane as described in [1], wherein the concentration of pentafluoroethane in the mixed gas is in the range of 0.1 to 50% by volume.

[3] The process for recovering pentafluoroethane as described in [1] or [2], wherein the mixed gas is brought into contact with the chlorinated solvent at a temperature of the chlorinated solvent in the range of $-50$ to $50°$ C.

[4] The process for recovering pentafluoroethane as described in any one of [1] to [3], wherein the mixed gas is a gas separated during production of pentafluoroethane.

[5] The process for recovering pentafluoroethane as described in [4], wherein the mixed gas is a low-boiling fraction (C) occurring during the production of pentafluoroethane, the low-boiling fraction (C) being obtained by:

(A) separating and recovering a gas component (A) by distillation, the gas component (A) containing at least pentafluoroethane and a non-condensable gas; and (C) separating the gas component (A) into a high-boiling fraction (C) and a low-boiling fraction (C), the high-boiling fraction (C) being based on pentafluoroethane and the low-boiling fraction (C) containing pentafluoroethane and the non-condensable gas.

[6] The process for recovering pentafluoroethane as described in [4], wherein the mixed gas is a low-boiling fraction (C) occurring during the production of pentafluoroethane, the low-boiling fraction (C) being obtained by:

(A) separating and recovering a gas component (A) by distillation, the gas component (A) containing at least chloropentafluoroethane and pentafluoroethane;

(B) bringing the gas component (A) into contact with hydrogen in the presence of a catalyst to remove chloropentafluoroethane and to obtain a gas component (B) containing at least pentafluoroethane and hydrogen; and (C) separating the gas component (B) into a high-boiling fraction (C) and a low-boiling fraction (C), the high-boiling fraction (C) being based on pentafluoroethane and the low-boiling fraction (C) containing at least pentafluoroethane and hydrogen.

[7] The process for recovering pentafluoroethane as described in [4], wherein the mixed gas is a low-boiling fraction (C) and/or a low-boiling fraction (E) occurring during the production of pentafluoroethane, the low-boiling fraction (C) and the low-boiling fraction (E) being obtained by:

(A) separating and recovering a gas component (A) by distillation, the gas component (A) containing at least pentafluoroethane;

(C) separating the gas component (A) into a low-boiling fraction (C) and a high-boiling fraction (C), the low-boiling fraction (C) containing at least pentafluoroethane and the high-boiling fraction (C) being based on pentafluoroethane;

(D) bringing the high-boiling fraction (C) into contact with oxygen and/or an oxygen-containing compound in the presence of a catalyst to obtain a gas component (D); and (E) separating the gas component (D) into a high-boiling fraction (E) and a low-boiling fraction (E), the high-boiling fraction (E) being based on pentafluoroethane and the low-boiling fraction (E) containing at least pentafluoroethane, and oxygen and/or the oxygen-containing compound.

[8] The process for recovering pentafluoroethane as described in [4], wherein the mixed gas is a low-boiling fraction (C) and/or a low-boiling fraction (E) occurring during the production of pentafluoroethane, the low-boiling fraction (C) and the low-boiling fraction (E) being obtained by:

(A) separating and recovering a gas component (A) by distillation, the gas component (A) containing at least chloropentafluoroethane and pentafluoroethane;

(B) bringing the gas component (A) into contact with hydrogen in the presence of a catalyst to remove chloropentafluoroethane and to obtain a gas component (B) containing at least pentafluoroethane and hydrogen;

(C) separating the gas component (B) into a low-boiling fraction (C) and a high-boiling fraction (C), the low-boiling fraction (C) containing at least pentafluoroethane and hydrogen and the high-boiling fraction (C) being based on pentafluoroethane;

(D) bringing the high-boiling fraction (C) into contact with oxygen and/or an oxygen-containing compound in the presence of a catalyst to obtain a gas component (D); and (E) separating the gas component (D) into a high-boiling fraction (E) and a low-boiling fraction (E), the high-boiling fraction (E) being based on pentafluoroethane and the low-boiling fraction (E) containing at least pentafluoroethane, and oxygen and/or the oxygen-containing compound.

[9] The process for recovering pentafluoroethane as described in any one of [1] to [8], wherein the chlorinated solvent is at least one compound selected from the group consisting of dichloromethane, trichloromethane, tetrachloromethane, 1,1-dichloroethane, 1,1,1-trichloroethane, 1,1,1,2-tetrachloroethane, pentachloroethane, dichloroethylene, trichloroethylene and tetrachloroethylene.

[10] The process for recovering pentafluoroethane as described in any one of [1] to [9], wherein the non-condensable gas is at least one gas selected from the group consisting of hydrogen, nitrogen, oxygen and carbon monoxide.

[11] A process for producing pentafluoroethane, wherein the chlorinated solvent including pentafluoroethane that is obtained by the recovering process described in any one of [1] to [10] is used as a raw material of pentafluoroethane without separating pentafluoroethane.

[12] A process for producing pentafluoroethane, comprising the steps of:

(I) fluorinating tetrachloroethylene and then recovering a crude pentafluoroethane by distillation which contains at least chloropentafluoroethane and pentafluoroethane;

(II) bringing the crude pentafluoroethane into contact with hydrogen in the presence of a catalyst to remove chloropentafluoroethane, and then separating the product into a low-boiling fraction (II) and a high-boiling fraction (II), the low-boiling fraction (II) containing at least pentafluoroethane and hydrogen and the high-boiling fraction (II) being based on pentafluoroethane;

(III) bringing the high-boiling fraction (II) into contact with oxygen and/or an oxygen-containing compound in the presence of a catalyst, and then separating the product into a high-boiling fraction (III) and a low-boiling fraction (III), the high-boiling fraction (III) being based on pentafluoroethane and the low-boiling fraction (III) containing at least pentafluoroethane, and oxygen and/or the oxygen-containing compound;

(IV) bringing the low-boiling fraction (II) and/or the low-boiling fraction (III) into contact with a chlorinated solvent to allow the chlorinated solvent to absorb pentafluoroethane; and (V) subjecting the chlorinated solvent including pentafluoroethane to production of pentafluoroethane without separating pentafluoroethane to produce pentafluoroethane.

[13] The process for producing pentafluoroethane as described in [11] or [12], wherein the chlorinated solvent is tetrachloroethylene.

EFFECT OF THE INVENTION

According to the present invention, pentafluoroethane is recovered inexpensively from a mixed gas containing pentafluoroethane and a non-condensable gas. The chlorinated solvent containing pentafluoroethane that is recovered may be used as a raw material for the production of pentafluoroethane, and pentafluoroethane may be produced with industrial advantages.

PREFERRED EMBODIMENTS OF THE INVENTION

The present invention will be described in detail hereinbelow.

As described above, pentafluoroethane emissions are possible in various industrial fields, frequently not as pentafluoroethane itself but as a mixed gas with other compounds. The recovering process of the invention brings such mixed gas into contact with a chlorinated solvent to allow the chlorinated solvent to absorb pentafluoroethane, whereby pentafluoroethane is recovered from the mixed gas.

Examples of the mixed gases include those containing pentafluoroethane and non-condensable gases. As used herein, the non-condensable gases are gases that are not substantially condensed at temperatures and pressures in processes such as distillation, cooling and compression. Examples of the non-condensable gases include hydrogen, nitrogen, oxygen and carbon monoxide. The non-condensable gases may be used singly or in combination of two or more kinds. Preferably, the pentafluoroethane concentration in the mixed gases is in the range of 0.1 to 50% by volume. When the pentafluoroethane concentration is less than 0.1% by volume, the yield of pentafluoroethane per unit amount of the mixed gas is lowered and the cost is increased. When the concentration exceeds 50% by volume, the chlorinated solvent should often be increased to an undesirable level.

The recovering process of the invention may apply to mixed gases emitted in various industrial fields described above, as long as the mixed gases contain pentafluoroethane and non-condensable gases and, preferably, the pentafluoroethane concentration is in the aforesaid range. The process is suited for treating mixed gases that are separated or emitted during the production of pentafluoroethane. Although the mixed gases separated or emitted during the production of pentafluoroethane will greatly vary in pentafluoroethane concentration, the process of the invention can recover pentafluoroethane efficiently by appropriately selecting the type and temperature of the chlorinated solvent, and contact conditions.

The following describes the mixed gases separated or emitted during the production of pentafluoroethane based on production steps.

(1) Fluorination Step

Pentafluoroethane may be synthesized by fluorinating tetrachloroethylene or a fluoride thereof with hydrogen fluoride (HF) by known methods (for example, JP-A-H09-511515). Tetrachloroethylene is an organic material and can decompose slightly in the presence of oxygen or water. Therefore, it is stored in a closed vessel pressurized with nitrogen. When tetrachloroethylene is subjected to the production of pentafluoroethane, it is fed to a reaction vessel by means of a pump or the like through a pipe directly connected from the storage vessel to avoid any contact with atmospheric air. Nitrogen that is used during the store is dissolved in the tetrachloroethylene that is fed. HF is a highly corrosive substance and is stored in a closed vessel pressurized with nitrogen. Consequently, as with tetrachloroethylene, Nitrogen that is used during the store is dissolved in the HF.

Accordingly, pentafluoroethane obtained by the fluorination can contain nitrogen (non-condensable gas) that was present in the raw materials.

(2) Distillation Step

The fluorination produces pentafluoroethane as a mixture of intermediate tetrachloroethylene partial fluoride, unreacted raw materials (tetrachloroethylene and hydrogen fluoride), and by-product hydrogen chloride (HCl). Pentafluoroethane is separated and recovered from these compounds by an appropriate method, generally by distillation (for example, WO 96/11176). However, pentafluoroethane forms an azeotropic or pseudo azeotropic mixture with HF or HCl, and therefore these acidic components should be removed by pretreatment with water or an aqueous alkaline solution, in which non-condensable gases such as nitrogen and air are dissolved. Consequently, these non-condensable gases can mix in pentafluoroethane obtained by distillation.

(3) Purification Step I (Hydrogenolysis)

Pentafluoroethane often contains chloropentafluoroethane as impurity. (Hereinafter, pentafluoroethane containing chloropentafluoroethane will be referred to as crude pentafluoroethane.) It is difficult that the above distillation separates and removes chloropentafluoroethane. Chloropentafluoroethane may be removed by known hydrogenolysis in the presence of a catalyst (for example, JP-A-H08-301801). In the hydrogenolysis, chloropentafluoroethane is reacted with hydrogen and is hydrogenated, with formation of by-product HCl. The hydrogenolysis uses hydrogen in excess over chloropentafluoroethane contained in pentafluoroethane so that the reaction will proceed more dominantly. Consequently, the hydrogen used (non-condensable gas) is not fully consumed in the hydrogenolysis and remains in pentafluoroethane after the hydrogenolysis.

(4) Separation Step I

Pentafluoroethane obtained in the distillation step or the purification step I frequently contains non-condensable gases such as nitrogen and hydrogen. Pentafluoroethane containing such non-condensable gases is generally separated into a mixed gas (low-boiling fraction) and a high-boiling fraction by known methods such as cooling and compression. The low-boiling fraction contains pentafluoroethane and non-condensable gases, and the high-boiling fraction is based on pentafluoroethane. The high-boiling fraction is usually condensed and recovered.

(5) Purification Step II

The high-boiling fraction obtained in the separation step I often contains HFC other than pentafluoroethane as impurity. HFC may be reduced by bringing the high-boiling fraction into contact with oxygen and/or an oxygen-containing compound (for example, JP-A-2003-261476). Upon contact, HFC are reacted with oxygen and/or the oxygen-containing compound, producing by-products such as carbon dioxide. This reaction uses oxygen and/or the oxygen-containing compound in an amount more than necessary for the reaction with HFC contained in pentafluoroethane so that the reaction will proceed more dominantly. Consequently, the oxygen and/or the oxygen-containing compound used (non-condensable gas) is not fully consumed in the reaction with HFC and remains in pentafluoroethane after the reaction.

(6) Separation Step II

Pentafluoroethane containing non-condensable gases such as oxygen that is obtained in the purification step II is generally separated into a mixed gas (low-boiling fraction) and a high-boiling fraction by known methods such as cooling and compression as with the separation step I. The low-boiling fraction contains pentafluoroethane and non-condensable gases, and the high-boiling fraction is based on pentafluoroethane. The high-boiling fraction is usually condensed and recovered.

<Absorption Step>

The mixed gas (low-boiling fraction) containing pentafluoroethane and non-condensable gases that is obtained in the separation step I and/or the separation step II can greatly vary in pentafluoroethane concentration depending on separation conditions. As described above, the recovering process of the invention can suitably treat mixed gases having a pentafluoroethane concentration of 0.1 to 50% by volume.

Accordingly, the separation step I and/or the separation step II preferably yields a mixed gas having this pentafluoroethane concentration. Alternatively, the pentafluoroethane concentration may be adjusted in the above range after the mixed gas is obtained in the separation step I and/or the separation step II.

The mixed gas containing pentafluoroethane and non-condensable gases is brought into contact with a chlorinated solvent, whereby pentafluoroethane in the mixed gas is absorbed in the chlorinated solvent. Known gas-liquid contact methods may be used (for example, KAGAKU KOGAKU BINRAN (Chemical Engineering Handbook), revised sixth edition, pp. 588-626). Examples of the gas-liquid contact apparatuses include packed columns, wetted-wall columns, spray columns, cyclone scrubbers, venturi scrubbers, centrifugal absorption apparatuses, bubble columns, plate columns and bubble agitation tanks. Packed columns are preferable because of good gas-liquid contact efficiency.

The packed columns may be packed with resins, metals, carbons or porcelains resistant to the chlorinated solvents and passing gasses. Examples include Raschig rings, beryl saddles, Tellerette and cascade mini rings.

When the mixed gas is brought into contact with the chlorinated solvent, the temperature of the chlorinated solvent is preferably in the range of −50 to 50° C., more preferably −20 to 20° C. Cooling the chlorinated solvent at below −50° C. adds cooling energy cost. When the temperature of the chlorinated solvent exceeds 50° C., not only the non-condensable gases but also the chlorinated solvent itself are evaporated, often causing loss of the chlorinated solvent. The contact preferably takes place in an apparatus at an inner pressure of 0.1 to 2 MPa. Achieving a pressure less than 0.1 MPa or more than 2 MPa requires a low-pressure or high-pressure device.

Examples of the chlorinated solvents include dichloromethane, trichloromethane, tetrachloromethane, 1,1-dichloroethane, 1,1,1-trichloroethane, 1,1,1,2-tetrachloroethane, pentachloroethane, dichloroethylene, trichloroethylene and tetrachloroethylene. Of these, trichloroethylene and tetrachloroethylene are preferred. The chlorinated solvents may be used singly or in combination of two or more kinds.

The mass ratio (L/G) of the chlorinated solvents and the mixed gas that are brought into contact with each other may be selected from a wide range depending on the types of gases and contact conditions. In particular, the lower limit of the L/G ratio influences the efficiency of removing pentafluoroethane from the mixed gas. The upper limit is limited by the pentafluoroethane concentration in the chlorinated solvent recovered and the maximum liquid load of the absorption column used. In the invention, the L/G ratio is preferably in the range of 5/1 to 30/1.

In the absorption step, pentafluoroethane in the mixed gas is absorbed in the chlorinated solvent. The chlorinated solvent containing pentafluoroethane may be used as a raw material in the production of HFC such as pentafluoroethane, without any post-treatments, specifically separation and recovery of pentafluoroethane from the chlorinated solvent. In particular, the chlorinated solvent is preferably tetrachloroethylene, in which case the chlorinated solvent tetrachloroethylene is combined with pure tetrachloroethylene followed by fluorination to give pentafluoroethane. In the case of other chlorinated solvents, the solvents may be fluorinated to give fluorides. HFC obtained by substituting all the chlorine in the chlorinated solvents with fluorine have uses in widespread industrial fields as with pentafluoroethane.

EXAMPLES

The present invention will be described in greater detail by examples below, but it should be construed that the invention is in no way limited thereto.

[Emission Example of Exhaust Gas Containing Pentafluoroethane]

Tetrachloroethylene was fluorinated with hydrogen fluoride followed by distillation. Consequently, a crude pentafluoroethane containing a little chloropentafluoroethane was obtained. The crude pentafluoroethane was brought into contact with hydrogen in the presence of a catalyst. The reaction gas produced was introduced in a −30° C. storage tank at a pressure of 0.3 MPa, and the gas was separated into condensed pentafluoroethane (high-boiling fraction) and a mixed gas (low-boiling fraction) containing hydrogen and pentafluoroethane. The mixed gas was analyzed by gas chromatography, resulting in the following composition.

HFC-125: 30% by volume
$H_2$: 67% by volume
HCl: 3% by volume

Example 1

A SUS 316 absorption column that was cooled and 10 cm in inner diameter was packed with polyethylene Tellerette having an outer diameter of 1 inch, in a height of 1.2 m. From the top of the column, tetrachloroethylene (TCE) cooled to 0° C. was fed at 50 kg/h, and the mixed gas of Emission Example was fed from below the packing at 1 $Nm^3/h$. The gas and the liquid were brought into contact with each other. The inner pressure was kept at 0.3 MPa by means of a pressure control valve provided at a gas outlet at the top of the column. After 1 hour, the temperature in the column stabilized, and the gas and the liquid at the outlets at the top and bottom of the absorption column, respectively, were analyzed for composition by gas chromatography. The results are shown in Table 1. From the results, 90% of HFC-125 was found to be recovered relative to HFC-125 contained in the mixed gas (exhaust gas).

TABLE 1

| | Gas composition at outlet at column top (vol %) | Liquid composition at outlet at column bottom (mol %) |
|---|---|---|
| HFC-125 | 4.3 | 3.8 |
| $H_2$ | 95.2 | 0.0 |
| HCl | 0.4 | 0.4 |
| TCE | 0.1 | 95.8 |

INDUSTRIAL APPLICABILITY

The invention is useful for recovering pentafluoroethane which is widely used as low-temperature refrigerants, foaming agents, propellants and etching gases. The process of the invention enables economically advantageous production of pentafluoroethane. Pentafluoroethane produced by the process of the invention has a wide range of uses as low-temperature refrigerants, foaming agents, propellants and etching gases.

The invention claimed is:

1. A process for recovering pentafluoroethane, comprising bringing a mixed gas containing pentafluoroethane and a non-condensable gas into contact with a chlorinated solvent to allow the chlorinated solvent to absorb pentafluoroethane contained in the mixed gas,
    wherein the mixed gas is a gas separated during production of pentafluoroethane, and
    wherein the mixed gas is a low-boiling fraction (C) occurring during the production of pentafluoroethane, the low-boiling fraction (C) being obtained by:
        (A) separating and recovering a gas component (A) by distillation, the gas component (A) containing at least pentafluoroethane and a non-condensable gas; and
        (C) separating the gas component (A) into a high-boiling fraction (C') and a low-boiling fraction (C), the high-boiling fraction (C') being based on pentafluoroethane and the low-boiling fraction (C) containing pentafluoroethane and the non-condensable gas.

2. The process for recovering pentafluoroethane according to claim 1, wherein the concentration of pentafluoroethane in the mixed gas is in the range of 0.1 to 50% by volume.

3. The process for recovering pentafluoroethane according to claim 1, wherein the mixed gas is brought into contact with the chlorinated solvent at a temperature of the chlorinated solvent in the range of −50 to 50° C.

4. The process for recovering pentafluoroethane according to claim 1, wherein the mixed gas is a low-boiling fraction (C) occurring during the production of pentafluoroethane, the low-boiling fraction (C) being obtained by:
  (A) separating and recovering a gas component (A) by distillation, the gas component (A) containing at least chloropentafluoroethane and pentafluoroethane;
  (B) bringing the gas component (A) into contact with hydrogen in the presence of a catalyst to remove chloropentafluoroethane and to obtain a gas component (B) containing at least pentafluoroethane and hydrogen; and
  (C) separating the gas component (B) into a high-boiling fraction (C') and a low-boiling fraction (C), the high-boiling fraction (C') being based on pentafluoroethane and the low-boiling fraction (C) containing at least pentafluoroethane and hydrogen.

5. The process for recovering pentafluoroethane according to claim 1, wherein the mixed gas is a low-boiling fraction (C) and/or a low-boiling fraction (E) occurring during the production of pentafluoroethane, the low-boiling fraction (C) and the low-boiling fraction (E) being obtained by:
  (A) separating and recovering a gas component (A) by distillation, the gas component (A) containing at least pentafluoroethane;
  (C) separating the gas component (A) into a low-boiling fraction (C) and a high-boiling fraction (C'), the low-boiling fraction (C) containing at least pentafluoroethane and the high-boiling fraction (C') being based on pentafluoroethane;
  (D) bringing the high-boiling fraction (C') into contact with oxygen and/or an oxygen-containing compound in the presence of a catalyst to obtain a gas component (D); and
  (E) separating the gas component (D) into a high-boiling fraction (E) and a low-boiling fraction (E), the high-boiling fraction (E) being based on pentafluoroethane and the low-boiling fraction (E) containing at least pentafluoroethane, and oxygen and/or the oxygen-containing compound.

6. The process for recovering pentafluoroethane according to claim 1, wherein the mixed gas is a low-boiling fraction (C) and/or a low-boiling fraction (E) occurring during the production of pentafluoroethane, the low-boiling fraction (C) and the low-boiling fraction (E) being obtained by:
  (A) separating and recovering a gas component (A) by distillation, the gas component (A) containing at least chloropentafluoroethane and pentafluoroethane;
  (B) bringing the gas component (A) into contact with hydrogen in the presence of a catalyst to remove chloropentafluoroethane and to obtain a gas component (B) containing at least pentafluoroethane and hydrogen;
  (C) separating the gas component (B) into a low-boiling fraction (C) and a high-boiling fraction (C'), the low-boiling fraction (C) containing at least pentafluoroethane and hydrogen and the high-boiling fraction (C') being based on pentafluoroethane;
  (D) bringing the high-boiling fraction (C') into contact with oxygen and/or an oxygen-containing compound in the presence of a catalyst to obtain a gas component (D); and
  (E) separating the gas component (D) into a high-boiling fraction (E) and a low-boiling fraction (E), the high-boiling fraction (E) being based on pentafluoroethane and the low-boiling fraction (E) containing at least pentafluoroethane, and oxygen and/or the oxygen-containing compound.

7. The process for recovering pentafluoroethane according to claim 1, wherein the chlorinated solvent is at least one compound selected from the group consisting of dichloromethane, trichloromethane, tetrachloromethane, 1,1-dichloroethane, 1,1,1-trichloroethane, 1,1,1,2-tetrachloroethane, pentachloroethane, dichloroethylene, trichloroethylene and tetrachloroethylene.

8. The process for recovering pentafluoroethane according to claim 1, wherein the non-condensable gas is at least one gas selected from the group consisting of hydrogen, nitrogen, oxygen and carbon monoxide.

9. A process for producing pentafluoroethane, wherein the chlorinated solvent including pentafluoroethane that is obtained by the recovering process according to claim 1 is used as a raw material of pentafluoroethane without separating pentafluoroethane.

10. A process for producing pentafluoroethane, comprising the steps of:
  (I) fluorinating tetrachloroethylene and then recovering a crude pentafluoroethane by distillation which contains at least chloropentafluoroethane and pentafluoroethane;
  (II) bringing the crude pentafluoroethane into contact with hydrogen in the presence of a catalyst to remove chloropentafluoroethane, and then separating the product into a low-boiling fraction (II) and a high-boiling fraction (II), the low-boiling fraction (II) containing at least pentafluoroethane and hydrogen and the high-boiling fraction (II) being based on pentafluoroethane;
  (III) bringing the high-boiling fraction (II) into contact with oxygen and/or an oxygen-containing compound in the presence of a catalyst, and then separating the product into a high-boiling fraction (III) and a low-boiling fraction (III), the high-boiling fraction (III) being based on pentafluoroethane and the low-boiling fraction (III) containing at least pentafluoroethane, and oxygen and/or the oxygen-containing compound;
  (IV) bringing the low-boiling fraction (II) and/or the low-boiling fraction (III) into contact with a chlorinated solvent to allow the chlorinated solvent to absorb pentafluoroethane; and
  (V) subjecting the chlorinated solvent including pentafluoroethane to production of pentafluoroethane without separating pentafluoroethane to produce pentafluoroethane.

11. The process for producing pentafluoroethane according to claim 9, wherein the chlorinated solvent is tetrachloroethylene.

12. The process for producing pentafluoroethane according to claim 10, wherein the chlorinated solvent is tetrachloroethylene.

* * * * *